US00PP15628P2

(12) United States Plant Patent
Evers

(10) Patent No.: US PP15,628 P2
(45) Date of Patent: Mar. 8, 2005

(54) HYBRID TEA ROSE PLANT NAMED 'TAN99065'

(50) Latin Name: *Rosa hybrida*
Varietal Denomination: TAN99065

(75) Inventor: Hans-Jurgen Evers, Uetersen (DE)

(73) Assignee: Rosen Tantau Mathias Tantau, Uetersen (DE)

( * ) Notice: Subject to any disclaimer, the term of this patent is extended or adjusted under 35 U.S.C. 154(b) by 75 days.

(21) Appl. No.: 10/282,787

(22) Filed: Oct. 28, 2002

(51) Int. Cl.[7] ..... A01H 5/00
(52) U.S. Cl. ..... Plt./139

(58) Field of Search ..... Plt./139, 140, 130, Plt./131

(56) References Cited

PUBLICATIONS

UPOV–ROM, 2003/05, Plant Variety Database, GTI Jouve Retrieval Software, citation for 'TAN99065'.*

* cited by examiner

*Primary Examiner*—Howard J. Locker
(74) *Attorney, Agent, or Firm*—Klarquist Sparkman LLP

(57) ABSTRACT

A rose plant of the hybrid tea class notable by the contrast the slight red wine scent of its flowers, and the contrast between the color of the flowers and the color of the foliage as the flower opens.

2 Drawing Sheets

Genus and species: *Rosa hybrida.*
Variety denomination: 'TAN99065'.

SUMMARY OF THE INVENTION

The present invention relates to a new and distinct variety of hybrid tea rose plant named 'TAN99065', which was originated by me by crossing an unnamed variety with an unnamed variety.

BACKGROUND OF THE INVENTION

The primary objective of this breeding was to produce a new red hybrid tea rose variety having slight red wine scent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Difference in color of outer petals and inner sides gives extraordinary display of flower while opening; and
2. Slight red wine scent.

Asexual reproduction of this new variety by buddings, as performed at Uetersen, Germany, shows that the foregoing and all other characteristics and distinctions come true to form and are established and transmitted through succeeding propagations.

Comparison with Parents

The female parent has larger blossoms than 'TAN99065'. The male parent's blossoms are a darker red than those of 'TAN99065'.

Comparison with Similar Variety

'TANorelav' (not patented) has smaller blossoms of a darker red than 'TAN99065'.

BRIEF DESCRIPTION OF THE ILLUSTRATION

The accompanying illustrations show in

Figure 1:
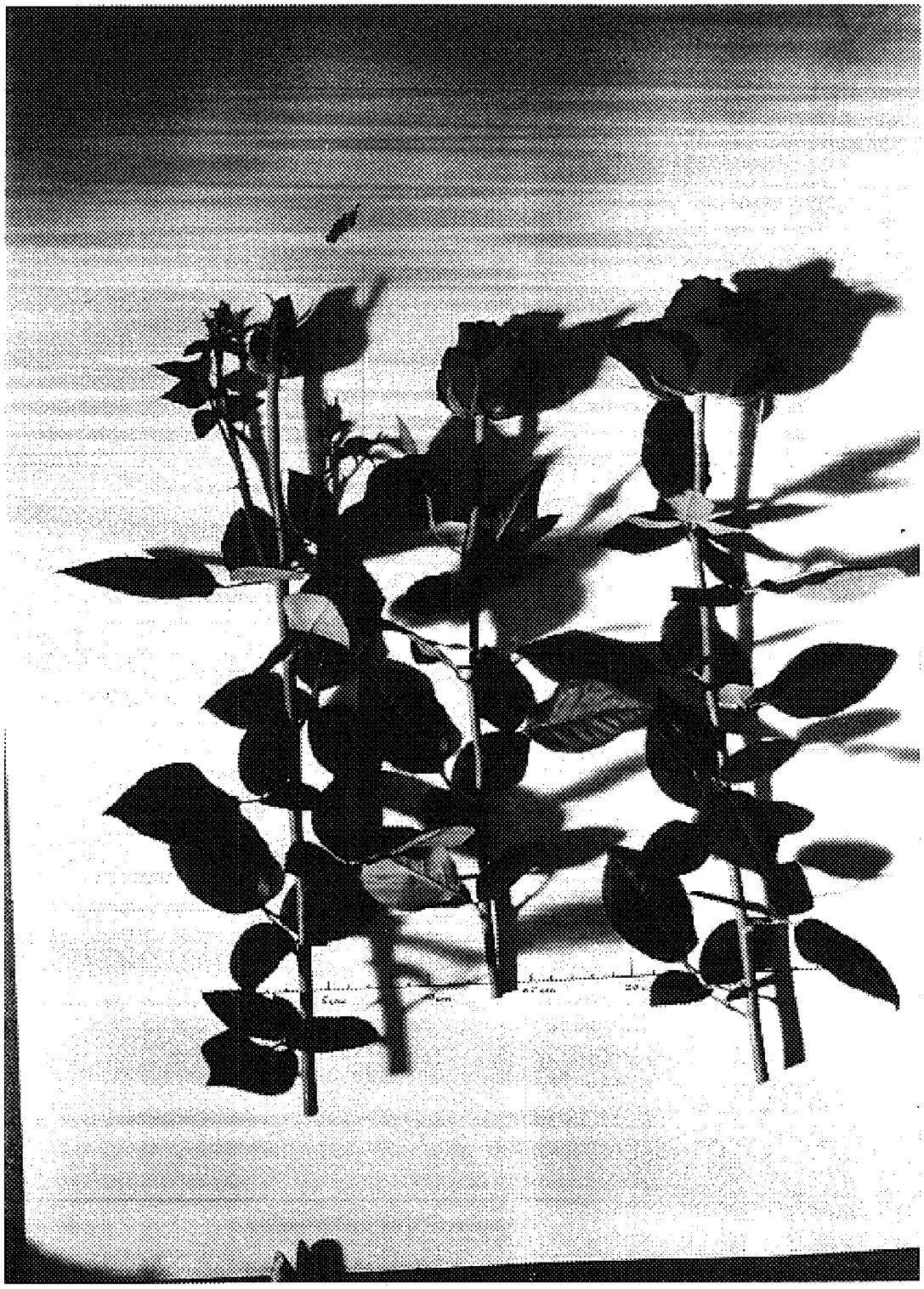
Figure 2:
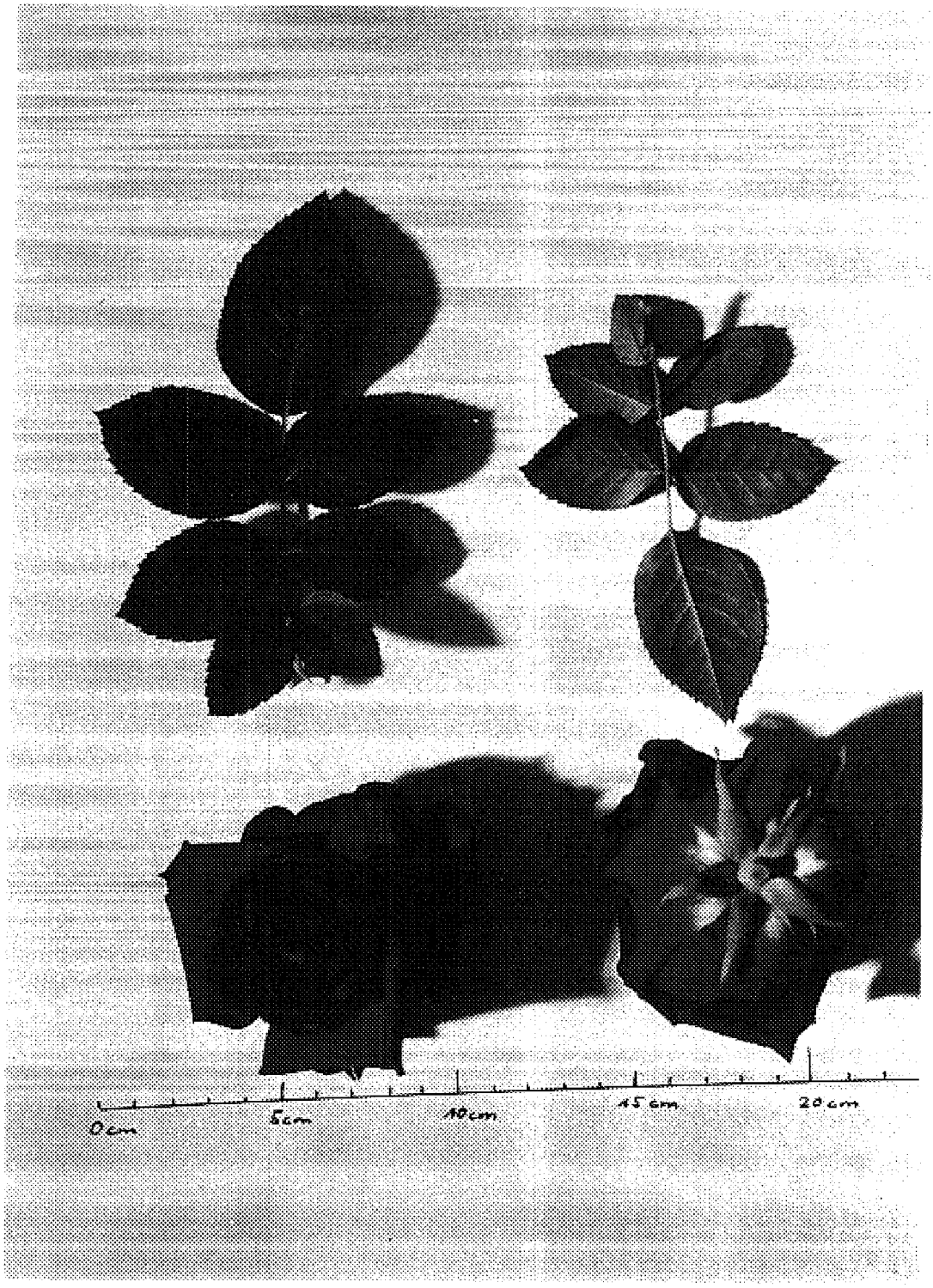

FIG. 1, stems of this new variety at different stages of development, from the bud stage to a fully opened flower, and in FIG. 2, views showing the leaf upper side and lower side and the top side and lower side of the bloom, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—Unnamed (unpatented).
*Pollen parent.*—Unnamed (unpatented).

FLOWER

Observations made from plants of 18 months of age grown in a greenhouse environment at Uetersen, Schleswig-Holstein, North Germany.

Blooming habit: Continuous.
Bud:
*Size.*—About 4.1 cm long and 2.4 cm in daimeter long when the petals start to unfurl.
*Form.*—The bud form is pointed ovoid.
*Color.*—When sepals first divide, bud color is bright red. When half blown, the upper sides of the petals are Red Group 45A; and the lower sides of the petals are Red Group 43D.
*Sepals.*—Color: Upper sides: Green Group 139A. Lower sides: Green Group 139C. Length: 4.6 cm.

Width: 0.9 cm. Shape: Pointed. Surface texture: Upper sides have a few hairs of Greyed-Green Group 192D. There are three heavily appendaged sepals. There are two unappendaged sepals with serrated edges.

*Receptacle.*—Color: Green Group 139D. Shape: Funnel. Size: Broad, about 3 cm long×3 cm wide. Surface: Smooth.

*Peduncle.*—Length: Medium, averaging about 10.4 cm. Surface: Smooth. Color: Green Group 145A. Strength: Erect.

Bloom:

*Size.*—Very large. Average open diameter is about 11.3 cm.

*Borne.*—Singly.

*Stems.*—Strength: Strong. Average length is about 70 cm, diameter about 0.5 cm.

*Form.*—When first open: Bloom is globular. Permanence: All petals curl.

*Petalage.*—Number of petals under normal conditions: 29.

*Color.*—The upper sides of the petals are Red Group 45A. The reverse sides of the petals are Red Group 54A. The base of each petal has a yellow spot of Yellow Group 21A. The major color on the upper side is Red Group 45A.

*Variegations.*—None.

*Discoloration.*—The general tonality at the end of the first day: No change. At the end of the third day: No change.

*Fragrance.*—Slight, alcoholic like red wine.

Petals:

*Texture.*—Leathery.

*Size.*—Width: 7.4 cm. Length: 6 cm.

*Shape.*—Oval.

*Margin.*—Not serrated but curled back. Apex Shape: Blunt, nearly semi-circular. Base Shape: Semi-circular.

*Form.*—Moderately quilled.

*Arrangement.*—Irregular.

*Petaloids.*—Number: 3.

*Persistence.*—Petals hang on and dry.

*Lastingness.*—On the plant: Long (about 14 days). As a cut flower: Long (about 14 days).

Reproductive parts:

*Stamens.*—Number: 87. Length: 0.7 cm. Anthers: Length: 0.3 cm. Color: Yellow-Orange Group 22A. Arrangement: Regular around styles. Filaments: Color: Yellow-Orange Group 22D. Length: 0.5 cm. Pollen: Color: Yellow-Orange Group 22A.

*Pistils.*—Number: 97. Length: 0.4 cm. Styles: Color: Red Group 46C. Length: 0.3 cm. Stigmas: Color: Yellow-Red Group 33A. Length: 0.1 cm.

*Hips.*—None produced.

PLANT

*Form.*—Upright, bushy, erect.

*Growth.*—Vigorous, upright.

*Mature plant.*—Height: 110 cm at one year of age. Width: 35 cm.

*Rootstock.*—*Rosa canina.*

Foliage: Number of leaflets on normal mid-stem leaves: 5.

*Size.*—Large (14 cm long×12 cm wide).

*Quantity.*—Normal.

*Color.*—New foliage: Upper side: Green Group 137B. Lower side: Green Group 138C. Old foliage: Upper side: Green Group 137A. Lower side: Green Group 138B.

Leaflets:

*Size.*—About 8 cm long×5 cm wide.

*Shape.*—Oval.

*Base shape.*—Blunt.

*Apex shape.*—Pointed.

*Texture.*—Upper side: Leathery.

*Edge.*—Serrated.

*Serrations.*—Single.

*Petiole.*—Color: Green Group 136A.

*Petiole rachis.*—Color: Green Group 135B. Underside: Smooth.

*Auricle shape, if present.*—Occasionally present. Length: 1 cm. Shape: Elongate and pointed.

*Stipules.*—Serrated. Length: about 1.4 cm.

*Disease resistance.*—Not tested.

*Pest persistence.*—Not tested.

*Vein color.*—Green Group 135C.

*Venation pattern.*—Veins are directed to the middle vein at the center of the leaflet.

Wood:

*New wood.*—Color: Green Group 136B. Bark: Smooth.

*Old wood.*—Color: Greyed-Orange Group 176A. Bark: Rough.

Prickles:

*Quantity.*—On main canes from base: 18 prickles per 15 cm stem length. On laterals from main canes: 3 prickles per 8 cm stem length.

*Form.*—Straight.

*Length.*—0.9 cm.

*Color when young.*—Greenish Brown.

*Color when mature.*—Greyed-Purple Group 187A.

Small prickles:

*Quantity.*—On main stalks: Few. On laterals: Few.

*Color.*—Yellow-Green Group 148A when young and Greyed-Purple Group 187A when mature.

Winter Hardiness: Not tested for zone hardiness, but plant is not frost resistant.

I claim:

1. A new and distinct variety of rose plant of the hybrid tea class, substantially as herein shown and described, characterized particularly by the slight red wine scent of its flowers, and the contrast between the color of the flowers and the color of the foliage as the flower opens.

* * * * *